US00PP10915P

United States Patent [19]

Zaiger et al.

[11] Patent Number: Plant 10,915

[45] Date of Patent: May 25, 1999

[54] INTERSPECIFIC TREE 'FLAVOR GEM'

[76] Inventors: Chris Floyd Zaiger, 929 Grimes Ave.; Gary Neil Zaiger, 1907 Elm Ave.; Leith Marie Gardner, 1207 Grimes Ave.; Grant Gene Zaiger, 4005 California Ave., all of Modesto, Calif. 95358

[21] Appl. No.: 08/977,901

[22] Filed: Nov. 25, 1997

[51] Int. Cl.[6] ..... A01H 5/00

[52] U.S. Cl. ..... Plt./180

[58] Field of Search ..... Plt./38.1, 33.1, Plt./39, 180, 184, 186

*Primary Examiner*—Howard J. Locker
*Assistant Examiner*—Anne Marie Grünberg

[57] ABSTRACT

A new and distinct variety of interspecific tree [(*Prunus salicina*×*Prunus armeniaca*)×*Prunus salicina*)×*Prunus salicina*)] which has the following unique combination of desirable features. The following features of the tree and its fruit are characterized with the tree budded on nemaguard rootstock, grown on Hanford sandy loam soil with Storie Index rating 95, in USDA hardiness zone 9, near Modesto, Calif., and with standard commercial cultural fruit growing practices, such as, pruning, thinning, spraying, irrigation, fertilization, etc:

1. Fruit with excellent flavor and eating quality.
2. Fruit having high soluble solids, average Brix 20.5°.
3. Heavy and regular production of fruit.
4. Precocious production of fruit, usually producing fruit in the second year after planting.
5. Maturity of fruit being relatively uniform throughout the tree.
6. The flavor of the fruit being distinctively different, with a blend between plum and apricot.
7. Vigorous, semi-spreading growth of tree.

1 Drawing Sheet

ORIGIN OF THE VARIETY

The present new and distinct variety of interspecific tree [(plumcot×plum)×plum)] was originated by us in our experimental orchard located near Modesto, Calif., between a selected seedling with field identification number 21GB794 and Royal Zee Plum (U.S. Plant Pat. No. 5,486). The female parent (21GB794) originated from a cross of a plumcot of unknown parentage with King David Plum (non-patented). A large group of these first generation, interspecific seedlings growing on their own roots, were planted and maintained under careful observation by us. One such seedling, which is the present variety, being especially desirable for its fruit characteristics was selected for asexual reproduction and commercialization.

ASEXUAL REPRODUCTION OF THE VARIETY

Asexual reproduction of the new and distinct variety of interspecific tree was by budding to nemaguard rootstock, as performed by us in our experimental orchard located near Modesto, Calif., and shows that all characteristics of the tree and its fruit run true to the original tree and are established and transmitted through succeeding asexual propagations.

SUMMARY OF THE VARIETY

A new and distinct variety of interspecific tree which is of medium size, vigorous, semi-spreading growth and is a productive and regular bearer of medium to large size, yellow flesh, freestone fruit. The fruit is further characterized by having firm flesh with excellent flavor and eating quality, having a good balance between sugar and acid, having high soluble solids of 20.5° Brix and relatively uniform maturity throughout the tree. The present interspecific tree is more spreading in growth, has a slightly rougher bark condition than most plum trees and, in comparison to the interspecific variety Flavor King (U.S. Plant Pat. No. 8,026), the fruit of the present new variety is approximately 1 week later in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a fruit divided in its suture plane to reveal flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree, its flowers, foliage and fruit, as based on observations of specimens grown near Modesto, Calif., with color terminology (except those in common terms) in accordance with Reinhold Color Atlas by A. Kornerup and J. H. Wanscher.

Tree:

*Size.*—Medium. Height of tree reduced to medium by pruning and heavy crop load.

*Vigor.*—Vigorous. Tree exhibits vigorous growth the first growing season of 4½ to 6 feet in height. Precocious production of fruit the second growing season has tendency to cause slower growth and semi-spreading condition due to weight of fruit on smaller limbs and scaffolds, even with selective pruning and thinning. Mature height pruned to 10 to 12 feet and 12 to 14 feet in width for economical harvesting of fruit.

*Form.*—Usually pruned to vase shape.

*Productivity.*—Productive — Fruit is reduced and spaced by thinning to produce marketable size. Number of fruit set varies with climatic conditions at bloom time.

*Bearer.*—Regular. Heavy fruit set is 1½ or more times the number desired for crop load.

*Density.*—Medium dense — pruning is necessary to prevent shading out of fruit wood and providing fruit with sunlight and heat units for higher soluble solids (Brix).

*Growth.*—Semi-spreading.

Trunk:

*Size.*—Large.

*Texture.*—Shaggy.

*Color.*—Brown to grayish brown (5-E-5) to (5-F-5).

Branches:

*Size.*—Medium.

*Texture.*—Smooth to medium shaggy, varies with age of growth.

*Lenticels.*—Medium number. Medium size.

*Color.*—Light brown to brown (5-D-6) to (5-E-6).

Leaves:

*Size.*—Medium to large. Average length 4½". Average width 1¾".

*Form.*—Oblanceolate.

*Margin.*—Finely serrate.

*Thickness.*—Medium.

*Surface.*—Smooth.

*Petiole.*—Average length ⅝". Average thickness 1/16".

*Glands.*—Globose. Number varies from 1 to 3. Average number 2. Located on upper portion of petiole and lower portion of leaf blade.

*Color.*—Upper surface — green to dark green (29-F-7) to (29-F-8). Lower surface — light green to green (29-E-6) to (29-E-7).

Flower buds:

*Size.*—Medium.

*Length.*—Medium.

*Form.*—Plump.

Flowers:

*Size.*—Large. ⅞" to 1" in diameter. Petals only slightly curved toward center when anthers dehisce. Pistil is approximately same height as anthers.

*Pollen.*—Present.

*Blooming period.*—Date of first bloom: Feb. 15, 1996. Date of last bloom: Feb. 24, 1996. Varies slightly with climatic conditions. Color White.

Fruit:

*Maturity when described.*—Firm ripe.

*Date of first picking.*—Aug. 12, 1996.

*Date of last picking.*—Aug. 18, 1996. Varies slightly with climatic conditions.

*Size.*—Medium. Average diameter axially 2⅝". Average transversely in suture plane 2⅜". Average weight 114 grams, varies from 100 to 140 grams. Varies slightly with number of fruit per tree, soil type, climatic conditions and cultural practices.

*Form.*—Nearly globose, slightly elongated in suture plane.

*Suture.*—Shallow, extends from base to apex.

*Ventral surface.*—Nearly rounded.

*Apex.*—Rounded.

*Base.*—Retuse.

*Cavity.*—Rounded to slightly elongated in suture plane. Average depth ¼". Average breadth ⅜".

Stem:

*Size.*—Medium. Average length 9/16". Average width 5/64".

*Color.*—Color varies from light brown to brown (5-D-4) to (5-E-5).

Flesh:

*Ripens.*—Evenly.

*Texture.*—Firm, fruit has slight give to pressure due to pit cavity.

*Fibers.*—Small, tender.

*Aroma.*—Slight.

*Amydgalin.*—Wanting.

*Eating quality.*—Excellent, good balance between sugar and acid.

*Flavor.*—Excellent.

*Color.*—Yellowish white near pit cavity (4-A-2) to light yellow near skin surface (4-A-4). Pit cavity grayish yellow (4-B-4).

Skin:

*Thickness.*—Medium.

*Texture.*—Medium, tenacious to the flesh.

*Bloom.*—Moderate.

*Tendency to crack.*—None.

*Color.*—Light yellow to yellow ground color (4-A-3) to (4-A-4). Overspread with garnet red to violet brown (10-E-8) to (10-F-8). Portions of the fruit exposed to the sun have slightly greater enhancement of violet brown than fruit with less sunlight and in shaded areas of the tree. Small, randomly spaced, areas of ground color surface to give speckled pattern to skin.

Stone:

*Type.*—Freestone.

*Size.*—Medium. Average length ⅞". Average width ⅝". Average thickness ½".

*Form.*—Ovoid to obovoid.

*Base.*—Varies from straight to rounded.

*Apex.*—Acuminate, short, small.

*Surface.*—Very lightly pitted throughout, two long furrows, one on each side of suture plane, short, shallow furrows extending from base toward apex.

*Sides.*—Unequal, one side slightly larger.

*Tendency to split.*—None.

*Color.*—Light brown to brown (5-C-5) to (5-D-5).

Use: Dessert. Market, local and long distance.

Keeping quality: Good. Fruit stored well for 3 weeks in cold storage in post harvest trials.

Shipping quality: Good. Picking and packing of fruit gave minimal bruising or scarring of flesh or skin.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct interspecific tree, substantially as illustrated and described, characterized by its medium size, vigorous, semi-spreading growth and being a productive and regular bearer of firm, yellow flesh, freestone fruit; the fruit is further characterized by having a high degree of soluble solids (average 20.5° Brix), having excellent flavor and eating quality and, in comparison to the fruit of the interspecific variety Flavor King (U.S. Plant Pat. No. 8,026), the present variety is approximately 1 week later in maturity.

* * * * *

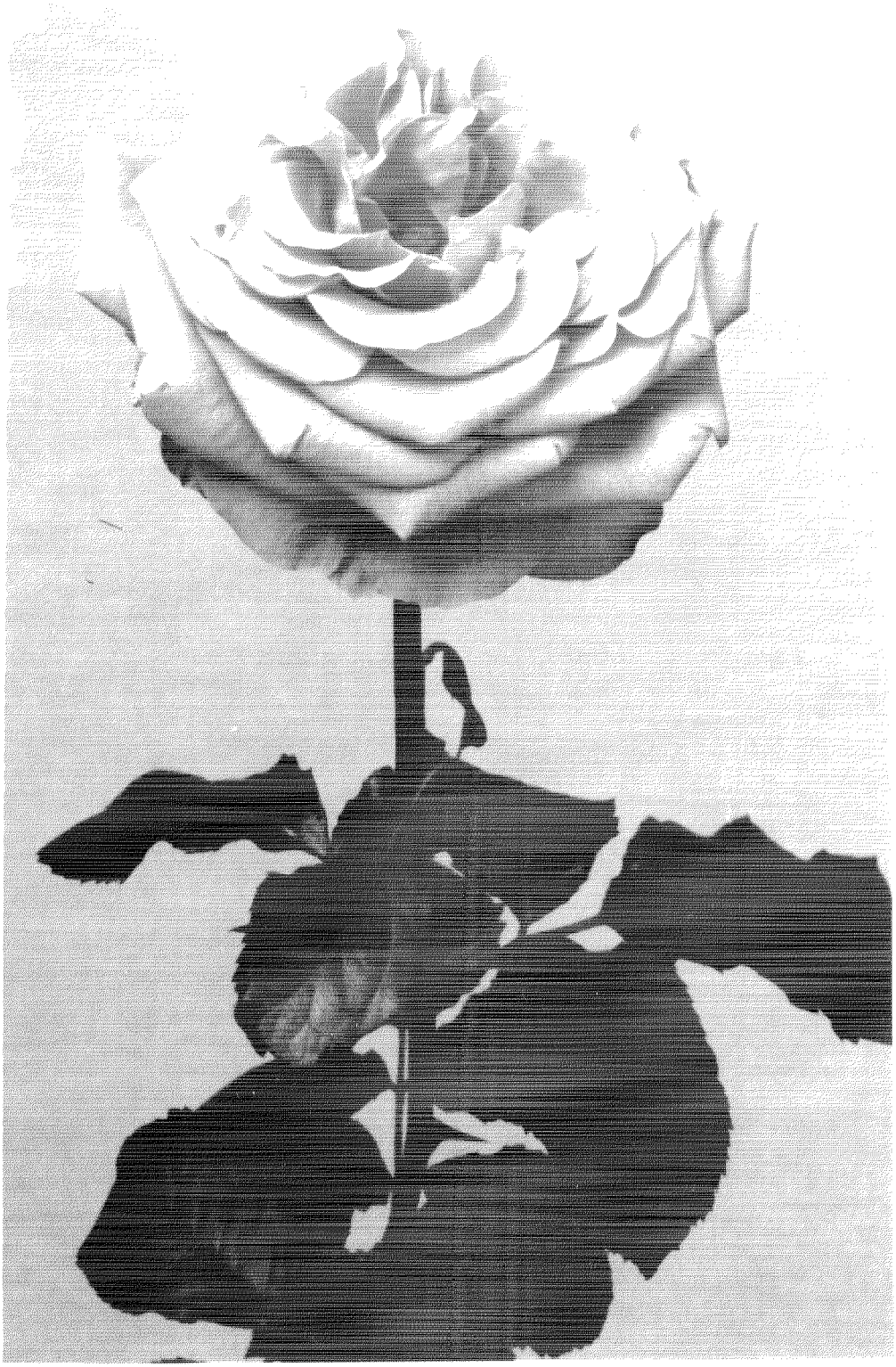

UNITED STATES PATENT AND TRADEMARK OFFICE

CERTIFICATE OF CORRECTION

PATENT NO. : PP 10,915
DATED : May 25, 1999
INVENTOR(S) : Chris Floyd Zaiger et al.

It is certified that error appears in the above-identified patent and that said Letters Patent is hereby corrected as shown below:

Drawing,
Replace drawing with correct drawing

Signed and Sealed this

Third Day of August, 2004

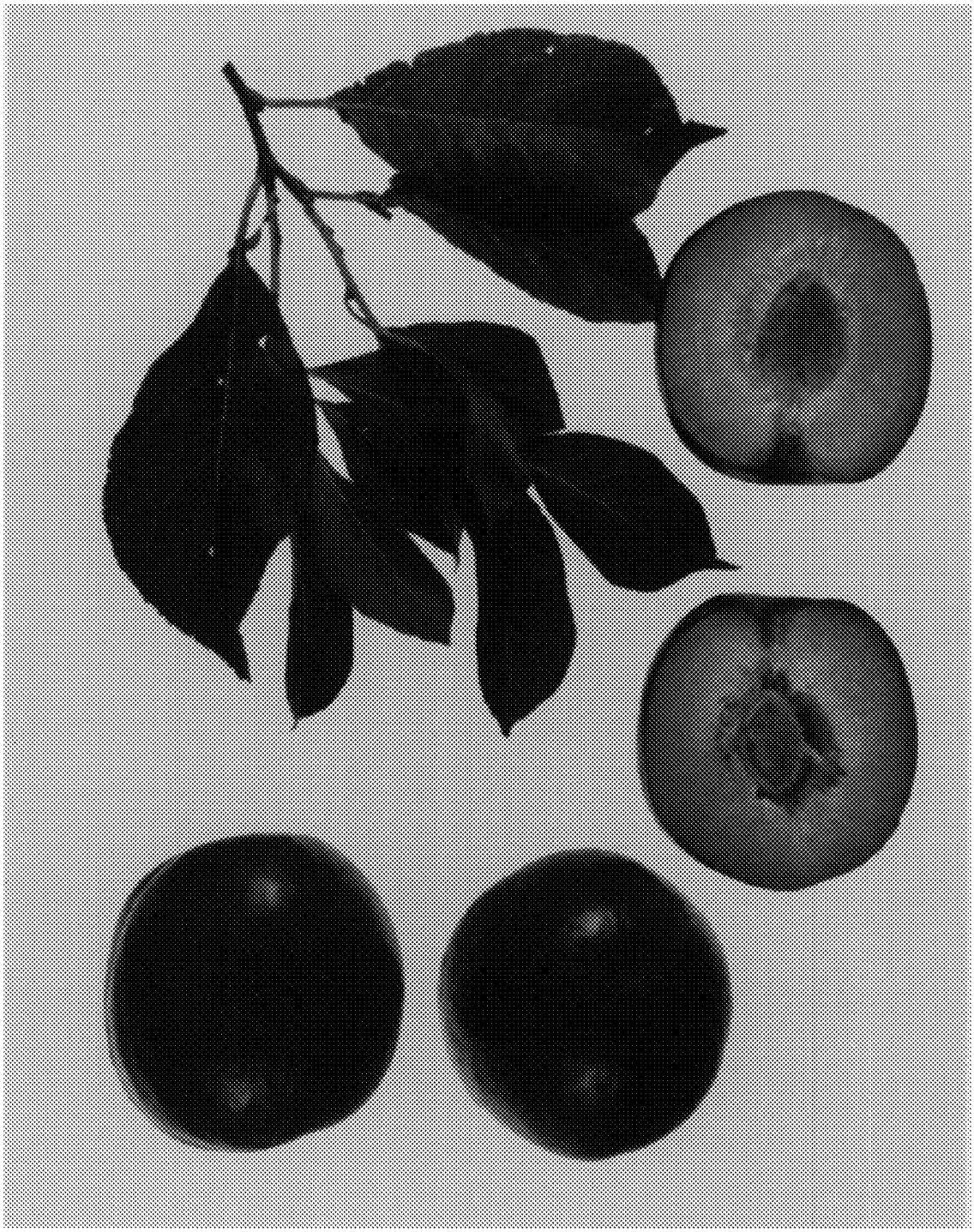

JON W. DUDAS
*Acting Director of the United States Patent and Trademark Office*